United States Patent [19]
Gelineau

[11] Patent Number: 5,800,564
[45] Date of Patent: Sep. 1, 1998

[54] ANKLE PROSTHESIS WITH ANGLE ADJUSTMENT

[76] Inventor: Roger Gelineau, 487 First Avenue, Ille des Chenes, Manitoba, Canada, R0H 0T0

[21] Appl. No.: 715,633

[22] Filed: Sep. 18, 1996

Related U.S. Application Data

[60] Provisional application No. 60/003,884 Sep. 18, 1995.

[51] Int. Cl.⁶ .................. A61F 2/62; A61F 2/66
[52] U.S. Cl. .................................. 623/38; 623/47
[58] Field of Search ..................... 623/38, 47, 53, 623/55, 39–46, 50–52; 602/27

[56] References Cited

U.S. PATENT DOCUMENTS

| | | |
|---|---|---|
| 2,749,557 | 6/1956 | Riddle. |
| 2,897,512 | 8/1959 | Sackett .................... 623/38 X |
| 5,052,375 | 10/1991 | Stark et al. .................. 601/34 |
| 5,156,630 | 10/1992 | Rappoport et al. ............ 623/47 |
| 5,571,206 | 11/1996 | Varn ........................ 623/27 |

FOREIGN PATENT DOCUMENTS

| | | | |
|---|---|---|---|
| 2148322 | 3/1973 | France. | |
| 330285 | 12/1920 | Germany ................... | 623/55 |
| 931184 | 6/1982 | U.S.S.R. .................. | 623/55 |
| 277760 | 9/1927 | United Kingdom. | |
| 2 080 115 | 2/1982 | United Kingdom .......... | 623/38 |
| 2177925 | 2/1987 | United Kingdom .......... | 623/47 |

OTHER PUBLICATIONS

Friddle's Orthopedic: "The Variable Motion Ankle Joint" (advertisement brochure).

*Primary Examiner*—David H. Willse
*Attorney, Agent, or Firm*—Adrian D. Battison; Murray E. Thrift

[57] ABSTRACT

An ankle prosthesis for attachment to a foot prosthesis and an upper leg portion includes a swivel connection allowing adjustment of the angle of a longitudinal axis of the foot prosthesis relative to a vertical axis of the leg portion. The adjustment is provided by a pair of plates lying in a common plane containing the longitudinal axis and the vertical axis which can rotate relative to one another and each includes a series of radial ribs allowing adjustment through predetermined angles.

6 Claims, 2 Drawing Sheets

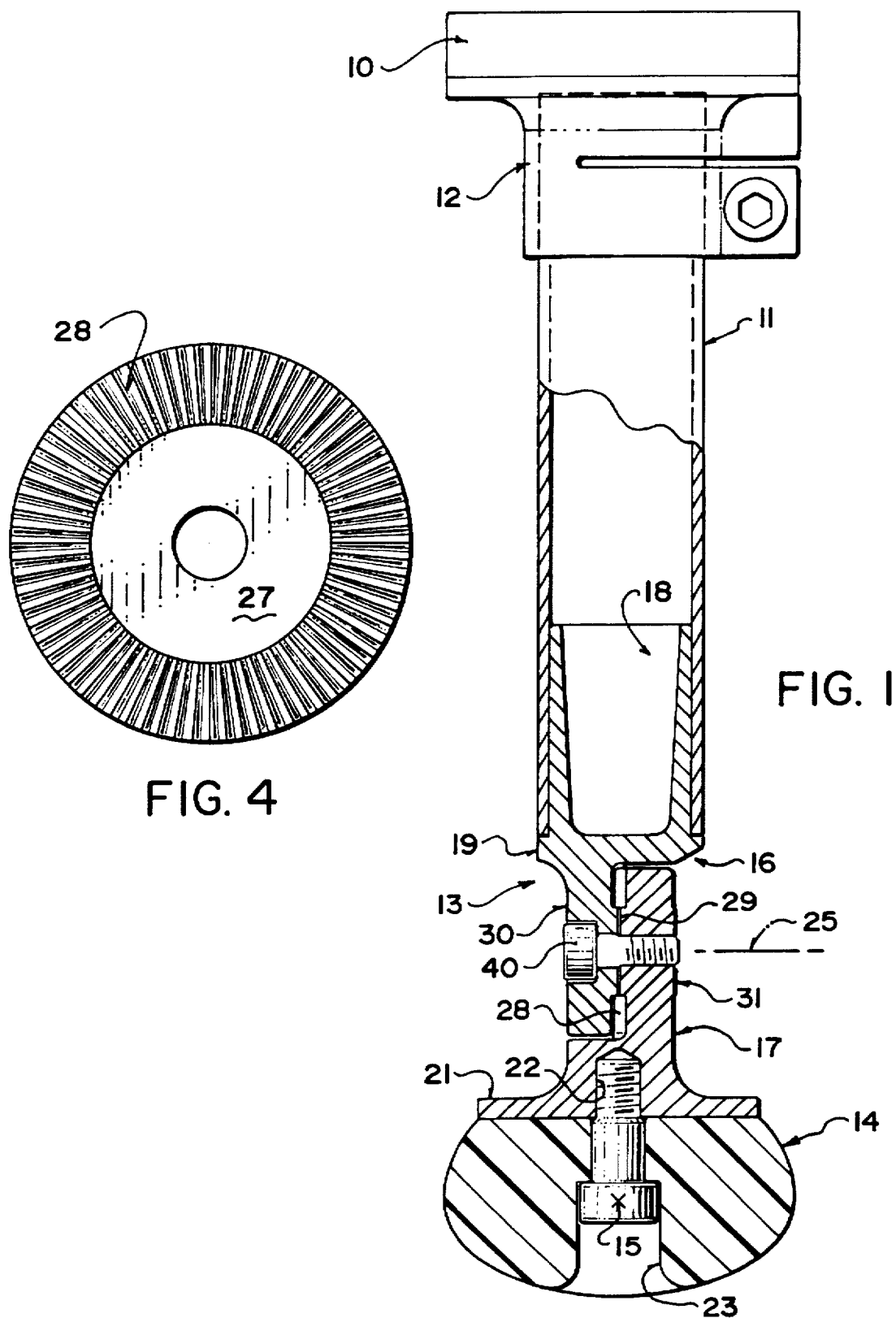

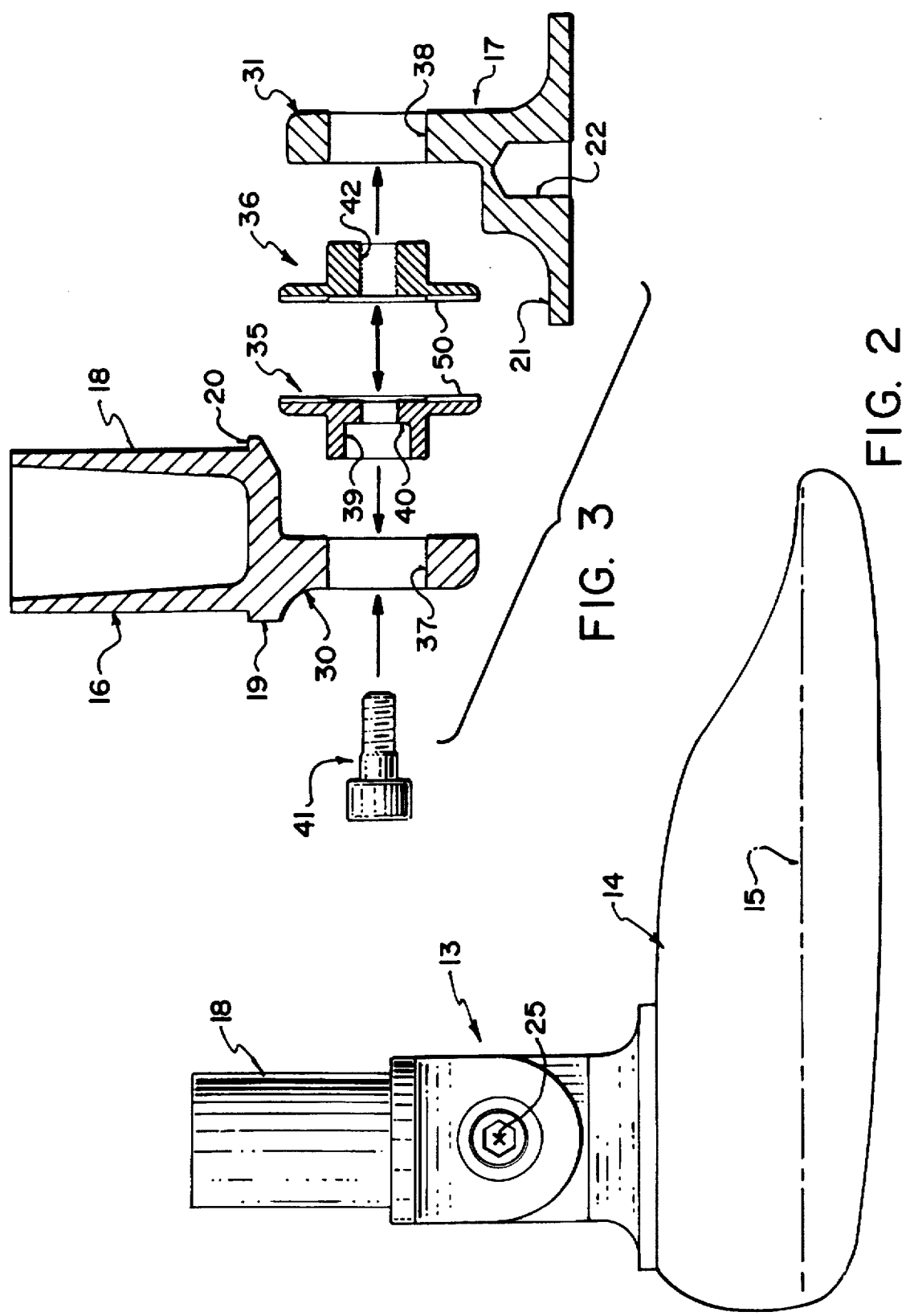

ANKLE PROSTHESIS WITH ANGLE ADJUSTMENT

This is a provisional application of Ser. No. 60/003,884, filed Sept. 18, 1995.

BACKGROUND OF THE INVENTION

This invention relates to an ankle prosthesis for mounting between a foot prosthesis and an upper coupling which attaches to the remaining leg portion of an amputee patient, the ankle prosthesis providing adjustment of the angle of the foot prosthesis relative to the coupling about an axis at right angles to a longitudinal axis of the foot.

A leg prosthesis for an amputee is generally adjusted so as to be suitable for a particular selected footwear with a predetermined heel height so that the position of the heel is adjusted for the wearer to match the existing leg of the patient. Generally when this adjustment is made, it is difficult or impossible to modify this adjustment should the patient wish to use the prosthesis with a different set of footwear of different heel height.

The heel height can vary dramatically between ski boots which have a negative angle between the heel and toe and high heeled shoes which have a relatively large positive angle between the heel and toe.

Some attempt has been made to provide adjustment of the position of the heel but generally this is done by an adjustment underneath the foot of the prosthesis which adjusts the height of the heel of the foot prosthesis relative to the leg prosthesis.

SUMMARY OF THE INVENTION

It is one object of the present invention, therefore, to provide an improved ankle prosthesis which allows simple ready adjustment of the angle of the foot prosthesis relative to the leg and particularly the coupling to the leg.

According to one aspect of the invention there is provided a leg prosthesis for attachment to a remaining leg portion of an amputee patient comprising: a foot prosthesis defining an elongate body having a longitudinal foot axis shaped to receive a shoe of the patient for application of pressure from the leg prosthesis to the ground through the shoe; an upper coupling for attachment to the remaining leg portion; and an ankle prosthesis located between the foot prosthesis and the upper coupling comprising a lower mounting bracket for attachment to the foot prosthesis and an upper mounting portion for attachment to the upper coupling; wherein the improvement comprises: a first swivel element mounted on the lower mounting bracket; a second swivel element mounted on the upper mounting portion; each of the swivel elements defining a planar abutment surface lying in a vertical plane longitudinal of the foot axis and surrounding an adjustment axis at right angles to the plane with the abutment surfaces facing one another; each of the abutment surfaces having a plurality of ribs extending radially of the adjustment axis at angularly spaced positions therearound with the angular spacing between the ribs being equal such that the ribs of the first swivel element intermesh with the ribs of the second swivel element; and means for clamping the swivel elements together to hold the ribs intermeshed, the clamping means being releasable and reengageable to allow rotation of the first swivel element relative to the second swivel element by an angle which a whole number multiple of the angular spacing of the ribs.

One embodiment of the invention will now be described in conjunction with the accompanying drawings in which:

BRIEF DESCRIPTION OF THE DRAWINGS

FIG. 1 is a part cross-sectional view of a leg prosthesis including the ankle prosthesis of the present invention.

FIG. 2 is side elevational view of the ankle prosthesis of FIG. 1.

FIG. 3 is an exploded view of the ankle prosthesis of FIG. 1.

FIG. 4 is a front elevational view of the abutment surface of one of the disks.

In the drawings like characters of reference indicate corresponding parts in the different figures.

DETAILED DESCRIPTION

The leg prosthesis as shown complete in FIG. 1 includes an upper connecting portion schematically indicated at 10 for connection to the remaining leg portion of an amputee patient. The upper coupling 10 can include a knee prosthesis if required for the amputee or may be simply a cup for attachment to a below knee amputee. This element is shown only schematically since it is well known to one skilled in the art.

The leg prosthesis further includes a tube 11 forming an elongate element defining the shin section of the prosthesis. At the top of the tube is provided a clamp assembly 12 attaching in known manner to the coupling 10.

The tube 11 is mounted on the ankle prosthesis generally indicated at 13. At the bottom of the ankle prosthesis is provided a foot prosthesis 14 which a shaped element simulating approximately a foot with a longitudinal axis 15 along the length of the foot.

The ankle prosthesis 13 includes an upper mounting portion 16 and a lower mounting bracket 17. The upper mounting portion 16 includes a sleeve 18 mounted on the upper face of a flange 19 and extending upwardly therefrom so as to receive the lower end of the tube 11 as a fixed element thereon with the end of the tube abutting a shoulder 20 defined by the flange 19 around the sleeve 18.

The lower mounting bracket 17 includes a base flange 21 with a central threaded opening 22 for receiving a screw 23 which attaches the foot prosthesis to the base flange 21 in fixed position relative thereto.

Each of the upper mounting portion 16 and the lower mounting bracket 17 includes a swivel element so that the position of the lower mounting bracket relative to the upper mounting portion can be adjusted in an angular direction about an adjustment axis 25 which is at right angles to the longitudinal axis 15 of the foot.

Each of the swivel members comprises a disk shaped element which provides a generally circular abutment surface. Each of the circular abutment surfaces lies in a plane parallel to the longitudinal axis 15 of the foot. Each of the abutment surfaces includes a plurality of ribs as best shown in FIG. 4 in which the abutment surface is indicated at 27 and the ribs at 28. The ribs are of triangular shape in cross section so that the ribs of one abutment surface intermesh with the ribs of the opposed abutment surface. The abutment surfaces lie on a center plane of the ankle prosthesis which plane is indicated at 29 in FIG. 1.

Thus the upper mounting portion 16 includes a swivel member indicated at 30 which is positioned wholly on one side of the central plane 29 and forms a disk extending downwardly from the bottom of the flange 19. Similarly the swivel member of the lower mounting bracket includes a disk extending upwardly from the flange 21 that disk indicated at 31 and lying wholly on a side of the plane 29 opposite to the disk 30.

In the preferred arrangement the upper mounting portion is cast as an integral body including the disk 30, the flange 19 and the sleeve 18. Similarly the lower mounting bracket is cast as an integral body including the flange 21 and the disk 31.

The teeth or ribs on the abutment surfaces are formed any suitable technique. In a preferred arrangement the ribs or teeth are formed by casting directly with the casting of the body itself. In an alternative arrangement the teeth are formed by cold forming or pressing of the teeth into a smooth surface formed in the casting process.

In a yet further arrangement shown best in FIG. 3, the teeth are formed on two separate disks 35 and 36 which are press fit into openings 37 and 38 respectively in the disks 30 and 31. Thus each of the disks 30 and 31 includes a relatively large opening. The insert 35 is formed with an internal bore 39 defining a shoulder 40 against which the head of a bolt 41 abuts. The insert 36 includes a smaller bore 42 which is threaded with a female screw thread to engage a male thread on the bolt 41.

With the inserts 35 and 36 pressed into place within the bores 37 and 38, the inserts define the abutment surfaces indicated at 50 carrying the teeth or ribs thereon in radial direction thereon at angularly spaced positions thereon.

The bolt 41 acts as a clamping arrangement to clamp the swivel members in fixed position.

The teeth or ribs 28 on the abutment surfaces provide an equally spaced arrangement around the abutment surface in the form of the annulus best shown in FIG. 4. In the preferred arrangement the spacing of the teeth is at five degree angular spacing. In this way the clamping bolt 41 can be released and the swivel members rotated each relative to the other by one or more teeth to provide an angular adjustment which is a whole number multiple of the angle between each tooth and the next which is perfectly five degrees.

The ankle therefore prosthesis therefore allows the angle of the foot relative to the tube 11 to adjusted to accommodate different height of heel for the wearer without adjusting the height of the heel of the foot prosthesis itself relative to the ankle prosthesis.

Important factors concerning the operation of the above device are as follows.

1. The relatively small angle of five degree increments allows effective adjustment to accommodate different footwear from ski boots to a relatively high heels.
2. The swivel elements are manufactured of a material such as 6061T6 aluminum which has sufficient strength to provide a rigid coupling when clamped while accommodating the forces involved in a patient weighing for example up to 200 pounds applying a load to the forward end of the foot prosthesis.
3. The design will accommodate up to 90 per cent of lower limb amputees and is adaptable up to 90 per cent of prosthetic systems.
4. The adjustment allows a range of angles to accommodate from a ski boot through a flat shoe up to a three and a half inch heel.

Since various modifications can be made in my invention as herein above described, and many apparently widely different embodiments of same made within the spirit and scope of the claims without departing from such spirit and scope, it is intended that all matter contained in the accompanying specification shall be interpreted as illustrative only and not in a limiting sense.

I claim:

1. A leg prosthesis for attachment to a remaining leg portion of an amputee patient comprising:

a foot prosthesis defining an elongate body having a lower surface for engaging the ground, an upper surface generally parallel to the lower surface and two generally upstanding side surfaces each on a respective side of the body so that the body is shaped to simulate a foot and to receive a shoe of the patient for application of pressure from the leg prosthesis to the ground through the shoe;

an upper coupling for attachment to the remaining leg portion;

and an ankle prosthesis located between the foot prosthesis and the upper coupling, the ankle prosthesis comprising:

a lower mounting bracket attached to the upper surface of the foot prosthesis and having a first swivel element standing upwardly therefrom;

an upper mounting portion for attachment to the upper coupling and having a second swivel element mounted thereon and extending downwardly therefrom for co-operation with the first swivel element;

the swivel elements defining co-operating abutment surfaces lying in a vertical plane longitudinal of the foot prosthesis and located between the side surfaces;

the swivel elements being mounted for relative rotation about an adjustment axis at right angles to the vertical plane;

each of the abutment surfaces having a plurality of ribs thereon, the ribs being raised in a direction longitudinal of the adjustment axis toward the other of the abutment surfaces and the ribs extending radially of the adjustment axis at angularly spaced positions therearound;

the ribs of the abutment surface of the first swivel element being arranged to intermesh with the ribs of the abutment surface of the second swivel element;

and means for clamping the abutment surfaces of the swivel elements together to hold the raised ribs in an intermeshed relationship to maintain the swivel elements against said relative rotation at a selected angle around the adjustment axis;

the clamping means being temporarily releasable to a distance to release the ribs from said intermeshed relationship to allow adjustment rotation of the first swivel element relative to the second swivel element through an angle which is a whole number multiple of the angular spacing of the ribs.

2. The improvement according to claim 1 wherein the ribs of each of the abutment surfaces are triangular in cross-section.

3. The improvement according to claim 1 wherein each abutment surface has an inner circular portion surrounding the adjustment axis which is smooth so as to be free from the ribs and an outer annular portion which is covered by the ribs.

4. The improvement according to claim 2 wherein each abutment surface has an inner circular portion surrounding the adjustment axis which is smooth so as to be free from the ribs and an outer annular portion which is covered by the ribs.

5. The improvement according to claim 1 wherein the lower mounting bracket comprises a substantially planar mounting flange with the first swivel element integrally formed with flange and standing upwardly therefrom on one side face of the flange with the abutment surface lying in a plane at right angles to the mounting flange with the plane intersecting with the mounting flange along a center line thereof.

6. The improvement according to claim 1 wherein the upper mounting portion comprises a substantially planar mounting flange with the second swivel element integrally formed with flange and standing upwardly therefrom on one side face of the flange with the abutment surface lying in a plane at right angles to the mounting flange with the plane intersecting with the mounting flange along a center line thereof and a sleeve mounted on the face of the flange opposite to the second swivel element.

* * * * *